US006613303B1

(12) United States Patent
Hess et al.

(10) Patent No.: US 6,613,303 B1
(45) Date of Patent: Sep. 2, 2003

(54) HIGHLY RADIOACTIVE MINIATURIZED CEREMIC STRONTIUM 90 RADIATION SOURCES AND METHOD FOR THE PRODUCTION THEREOF

(75) Inventors: André Hess, Berlin (DE); Teja Reetz, Schöneiche (DE)

(73) Assignee: Eurotope Entwicklungsgesellschaft für Isotopentechnologien mbH, Berlin (DE)

( * ) Notice: Subject to any disclaimer, the term of this patent is extended or adjusted under 35 U.S.C. 154(b) by 0 days.

(21) Appl. No.: 09/554,008

(22) PCT Filed: Sep. 13, 1999

(86) PCT No.: PCT/EP99/06732

§ 371 (c)(1),
(2), (4) Date: Jul. 10, 2000

(87) PCT Pub. No.: WO00/22628

PCT Pub. Date: Apr. 20, 2000

Related U.S. Application Data

(60) Provisional application No. 60/106,700, filed on Nov. 2, 1998.

(30) Foreign Application Priority Data

Oct. 13, 1998 (DE) ........................................ 198 48 312

(51) Int. Cl.[7] ....................... A61K 51/00; A61M 36/14; C01F 13/00; C01F 15/00; C01G 43/00; C01G 56/00; C01G 57/00; G21C 21/00

(52) U.S. Cl. ..................... 424/1.11; 424/1.61; 423/249; 264/0.5

(58) Field of Search .......................... 264/0.5; 423/249; 424/1.11, 1.25, 1.61

(56) References Cited

U.S. PATENT DOCUMENTS 3,944,438 A 3/1976 Hursen et al.
4,061,583 A 12/1977 Murata et al.
5,032,375 A * 7/1991 Lerot et al. ................. 423/598

OTHER PUBLICATIONS

Domen et al. "Photocatalytic Decomposition of Water Vapor on an NiO–SrTiO3 Catalyst". J. Chem. Soc., Chem. Commun. (12), 543–4, 1980.*

Kasimov et al. "Synthesis of Strontium Titanates". Zh. Neorg. Khim., 22(3), 616–18. 1997.*

Smith et al. "Preparation and Characterization of Alkoxy–Derived SrZrO3 and SrTiO3". J. Amer. Ceram. Soc., 53(2), 91–6. 1970.*

Kao et al. "Preparation and Electrical Characterization of Strontium Titanate Ceramic from Titanyl Acylate Precursor in Strong Alkaline Solution". Ceram. Int., 22(1), 57–66. 1996.*

Tuttle et al. "Powder Synthesis of Strontium Titanate Boundary Layer Capacitor Materials". Ceram. Trans., 1(Ceram. Powder Sci. 2, Pt. A), 62–9. 1988.*

Thampi et al. "Preparation of Strontium Titanate by Sol–Gel Techniques for the Photoinduced Production of Hydrogen and Surface Peroxides from Water". J. Chem. Soc, Faraday Trans. 1, 84(5), 1703–12. (1988).*

Braustein et al. "The Processes of Fromation and Epitaxial Alignment of STrontium Titanate Thin Films Prepared by Metalorganic Decomposition". J. Appl. Phys., 73(2), 961–70. 1998.*

Patent Abstract of Japan, vol. 13, No. 260, JP 01 061354 A, Mar. 08, 1989.

Database WPI, XP002123368, JP 09 077516 A, Mar. 25, 1997.

Database WPI, XP002123369, JP 55 029007 B, Jul. 31, 1980.

Database WPI, XP002123370, JP 48 100599 A, Dec. 19, 1973.

Database WPI, XP002123371, JP 48 066600 A, Sep. 12, 1973.

Registry of Radioactive Sealed Sources and Devices (1998).

Registry of Radioactive Sealed Sources and Devices (1982).

* cited by examiner

*Primary Examiner*—Sreeni Padmanabhan
*Assistant Examiner*—Lauren Q. Wells
(74) *Attorney, Agent, or Firm*—Birch, Stewart, Kolasch & Birch, LLP

(57) ABSTRACT

The present invention relates to highly radioactive, miniaturized, cylindrical strontium 90 titanate, strontium 90 zirconate, and strontium 90 silicate radiation sources having an activity exceeding 25 mCi/mm$^3$, preferably ≧30 mCi/mm$^3$, and a diameter less than 0.7 mm, preferably less than 0.4 mm. Another subject of this invention is a method for the production of these extremely small, but highly radioactive radiation sources.

18 Claims, No Drawings

HIGHLY RADIOACTIVE MINIATURIZED CEREMIC STRONTIUM 90 RADIATION SOURCES AND METHOD FOR THE PRODUCTION THEREOF

This application is the national phase under 35 U.S.C. §371 of PCT International Application No. PCT/EP99/06732 which has an International filing date of Sep. 13, 1999, which designated the United States of America and claims benefit of Ser. No. 60/106,700 filed Nov. 2, 1998.

The present invention relates to highly radioactive, miniaturized, cylindrical strontium 90 titanate, strontium 90 zirconate, and strontium 90 silicate radiation sources having an activity exceeding 25 $mCi/mm^3$, preferably ≧30 $mCi/mm^3$, and a diameter less than 0.7 mm, preferably less than 0.4 mm. Another subject of this invention is a method for the production of these extremely small, but highly radioactive radiation sources.

In the following description, strontium 90 titanate is also referred to as $^{90}SrTiO_3$, strontium 90 zirconate as $^{90}SrZrO_3$, and strontium 90 silicate as $^{90}SrSiO_3$.

With respect to medical applications, the importance of miniaturization of the radioactive radiation sources is steadily increasing. For example, in tumour therapy and intravascular brachytherapy, i.e. the exposure of the inner wall of blood vessels to radiation, inserted miniaturized sources are used.

There are essentially two known methods of producing miniaturized radiation sources of the strontium 90 isotope. In the production of tabular radiation sources, a mixed precipitation of $Ag_2CO_3/^{90}SrCo_3/TiO_2$ with subsequent malleabilization of the precipitate is used wherein the emerging silver cake is brought into the desired shape. Regarding the production of miniaturized, cylindrically shaped strontium 90 sources, it is known to soak a preformed carrier body consisting of titanium dioxide with a $^{90}Sr(NO_3)_2$ solution, to dry and then to anneal it at a temperature exceeding 1,000° C. In this process, insoluble strontium 90 titanate ($^{90}SrTiO_3$) is generated. These radiation sources are characterized by having an activity of only 5 to 7 mCi per $mm^3$. This activity and the resulting dose rate, however, are not sufficient, for instance, for the aforementioned medical applications. There still remains a need of having possibly small but highly radioactive strontium 90 radiation sources.

Therefore, it was an object of this invention to provide a manufacturing method for producing highly radioactive and very small strontium 90 radiation sources using a possibly automated or partly automated technique. In order to reach even very small blood vessels in medical applications, the diameter of the radiation source should be less than 0.6 mm.

The object of this invention is solved by a method for producing ceramic strontium 90 radiation sources wherein the aqueous solution of a strontium 90 salt is united with a titanium, zirconium, and/or silicon compound being in a dissolved state and the solution of one or more ammonium salts of carbonic acid and/or a low-molecular organic acid, the solvent is expelled from the mixture, the residue is calcinated and, after adding auxiliary agents, is transformed into a plastic state, the plastic matter is microextruded, the emerging thread is exposed to a sintering process and finally cut at the desired lengths so that miniaturized radiation sources are obtained which can be encapsulated in a manner known per se if necessary. It is also possible, of course, to first cut and then sinter the strontium 90 mass thread obtained. Below, the $^{90}SrTiO_3$, $^{90}SrSiO_3$, and $^{90}SrZrO_3$ bodies produced according to the present invention are also referred to as "radioactive ceramics".

The manufacturing method according to the present invention by which the radioactive ceramics is produced by microextrusion is advantageous in comparison with the conventional soaking technique in which pre-fabricated inactive ceramic carriers are soaked with the strontium 90 solution in that radiation sources having a higher Sr 90 portion (in the case of $^{90}SrTiO_3$, the density is ≧4 $g/cm^3$) can be produced. The method according to the present invention may (in part) be automated and remote-controlled. No grinding processes, no screening, no filtration processes, no spraying operations, and, except cutting, no finishing processes are necessary. The cylindrical sources are not manufactured as individual cylinders but as string (thread) which is cut in the raw or sintered state.

The initial compounds for the manufacturing method according to the invention are commercially available. For instance, strontium 90 nitrate having a concentration of 0.2 g solid matter/ml, which is commercially available and contains portions of barium nitrate and minor iron impurities, can be used as strontium 90 salt. The strontium 90 salt used may also be the salt of a low-molecular organic acid such as for instance $^{90}Sr$ formiate or $^{90}Sr$ acetate.

Although the present invention allows the use of water-soluble salts such as chlorides as titanium, zirconium, or silicon compounds, alcoholates are preferred. Mixtures of titanium, zirconium, and silicon alcoholates may also be used here so that mixed ceramics are generated, for instance comprising $^{90}SrSiO_3$ and $^{90}SrTiO_3$, or $^{90}SrSiO_3$ and $^{90}SrZrO_3$. The embodiment using either a titanium or a zirconium or a silicon alcoholate is preferred, however. According to the present invention, ethylates, propylates, butylates, the corresponding iso-compounds, or the corresponding mixed alcoholates are used as preferred alcoholates. Special preference is given to tetra-isopropylorthotitanate (TiPOT) in the production of $^{90}SrTiO_3$ ceramics. For producing $^{90}SrSiO_3$ ceramics, tetraethoxysilane (TEOS) is particularly preferred. For producing $^{90}SrZrO_3$ ceramics, zirconium (IV) propylate is particularly preferred. The alcoholates are, according to the present invention, preferably used in an anhydrous alcoholic solution.

As an ammonium salt, all those compounds may be used the anion of which is thermally separable or thermally decomposable and which form a hardly soluble compound with strontium, such as carbonate or oxalate. The ammonium may also be present in a substituted form as an organic ammonium compound. Ammonium compounds soluble in alcohol such as ammonium oxalate which may be used in a solution together with the silicon, titanium, and zirconium alcoholates are also suitable. In a preferred embodiment, $(NH_4)_2CO_3$ is used.

According to the present invention, the mol ratio of $^{90}Sr:Me:NH_4$ is 0.85-1:0.95–1.05:1.7–2, preferably 0.93:1:1.86, wherein Me means Ti, Zr, and/or Si.

The initial solutions described above are mixed by starting with the $^{90}Sr$ solution and homogenized, preferably by stirring. Thereafter, the solvent is mostly expelled and the residue calcinated, preferably at 650–1,000° C. wherein the duration period at this temperature is approximately one hour. The preferred calcination temperature ranges between 800–830° C., in particular preferably at 820–830° C.

The expulsion of the solvent may be accomplished by evaporation and/or sublimation.

Afterwards a plasticator is mixed into the calcinated mass. A number of recipes of plasticators for oxide ceramics are known which usually include organic auxiliary substances such as a solvent, a bonding agent, a softener, a lubricant, and a dispersion agent. One substance may also fulfil the function of several components.

An aqueous plasticator comprising a cellulosic derivative of a medium mol mass, a polysaccharide, a polyol, e.g. glycerol, and a polyelectrolyte has proved to be advantageous for the plastication of the strontium 90 mass according to the present invention. These auxiliary agents are added to the calcinated powder after cooling in a quantity ranging between 6 and 18 percent by weight in relation to the weight of the powder. Apart from these auxiliary agents being per se usual with respect to plastication, according to the present invention a silicon, titanium, and/or zirconium alcoholate in a quantity between 0.5 to 2 percent by weight is added to the calcinated powder during the plastication process. The alcoholates used may be the same as mentioned above in connection with the production of the initial mixture. In case of the use of TiPOT, the mass ratio of cellulosic derivative: polysaccharide:polyol:polyelectrolyte:TiPOT is 7–9:3.5–4.5:6–8:0.8–1.2:15–24, preferably 8:4:7:1:19. In case of the use of TEOS, the mass ratio of cellulosic derivative:polysaccharide:polyol:polyelectrolyte:TEOS is 7–9:3.5–4.5:6–8:0.8–1.2:20–30, preferably 8:4:7:1:25.

The crumbly mass mixed with the plasticator is then made smooth and pore-free by intense kneading and deaerating and in a final step is microextruded. For microextrusion devices may be used which operate in compliance with the principles of common capillary viscosimeters or common laboratory extruders.

The subsequent sintering of the strontium 90 ceramic string is preferably accomplished by slowly heating up to approximately 400° C. and then speeding up the heating process a little until the proper sintering temperature is reached which ranges between 1,260° C. and 1,420° C. In a most preferred embodiment heating up to approximately 400° C. is done by 1.5 K/min and then up to the sintering temperature by about 5 K/min. It has been found out that the preferred sintering temperature ranges between 1,370 and 1,390° C. The sintering process shall proceed for about one hour. Thereafter, the strontium 90 thread is cut to the desired lengths, for instance by laser cutting. The length of the radiation sources is preferably approximately 1.8 mm. Other lengths may of course also be realized.

The $^{90}SrTiO_3$, $^{90}SrZrO_3$, or $^{90}SrSiO_3$ radiation sources obtained are of sufficient stability and have densities $\geqq 80$ % of the crystallographic density which corresponds to a radioactivity >25 mCi/mm$^3$, preferably even $\geqq 30$ mCi/mm$^3$. The diameter obtained is less than 0.6 mm, preferably also less than 0.4 mm. The particularly preferred diameter of the sources produced according to the present invention is approximately 0.3 mm. Statistically, the strontium distribution lies within molecular ranges. The final products of the method according to the present invention are abrasion-proof; the strontium 90 is not washed out by water or other solvents. The final products are highly homogenous. If it is desired to further enhance homogenity, this can be accomplished by lyophilizing the initial mass after the expulsion of the solvent in an additional interim step and then calcinating the lyophilisate. The other steps of the method are performed as described above.

Beside the production method described above, radioactive strontium titanate, strontium zirconate, and strontium silicate radiation sources having an activity exceeding 25 mCi/mm$^3$, preferably $\geqq 30$ mCi/mm$^3$, and a diameter <0.7 mm, preferably <0.4 mm, most preferably <0.3 mm, constitute another object of the present invention. The cylindrical radiation sources according to the present invention may be encapsulated in a per se known manner in a material tolerated by the human body such as for instance stainless steel. This is accomplished by inserting the radioactive ceramics produced into a small tube which is closed on one end and sealing the opening on the other end by means of a lid. Preferably, said lid is laser-welded.

In order to improve the visibility of the radiation sources according to the present invention during the therapy in X-ray diagnostics, two tantalum cylinders having the same thickness as the ceramics may be inserted as X-ray markers at both ends, respectively, of the cylindrical radioactive ceramics into the small tube which is closed on one end. Then the tube is sealed by means of the lid as described above. In this manner, it is possible to show/determine the orientation of the radiation source because stainless steel and ceramics are invisible in X-ray diagnostics. Due to the extreme tininess of the radiation sources produced, it is not possible—as for instance in seeds for prostata cancer irradiation—to insert silver or gold threads as X-ray markers. With respect to the present case, the method using tantalum cylinders as described above hence provides an excellent solution.

IMPLEMENTATION EXAMPLE

Production of a cylindrical $^{90}SrTiO_3$ radiation source having a radioactivity of approximately 30 mCi/mm$^3$ wherein the diameter of the activity carrier is 0.26±0.01 mm.

1 ml of a $^{90}Sr(NO_3)_2$ solution with 0.2 g of solid matter comprising approx. 80% $^{90}Sr(NO_3)_2$, approx. 20% $Ba(NO_3)_2$ , and approx. 1% $Fe(NO_3)_3$ is filled into a platinum finger crucible having a capacity of 6 ml. While stirring, a solution of 285 mg tetra-iso-propyl orthotitanate in 0.3 ml ethanol is added. Immediately thereafter a solution of 90 mg $(NH_4)_2CO_3$ in 0.5 ml water is quickly added. Then stirring proceeds for about 15 minutes. Afterwards, the temperature is raised to reach 95° C. within 60 minutes to evaporize the solvent. For calcination, the temperature is then raised by approx. 500 K/h to reach 820° C. and kept at this level for about 60 minutes. After cooling down, as plasticator 6.2 mg cellulose, 3.1 mg polysaccharide, 5.2 mg glycerol, 0.5 mg polyelectrolyte (carboxylic acid batch), 20 $\mu$l tetra-iso-propyl orthotitanate, and 180 mg water are mixed with the mass. The mass is transferred from the platinum finger crucible into a pot press having a pot capacity of 6 ml and by the application of pressure pressed through a punched bottom having a diameter of 0.3 mm. The emerging thread is led back into the pot press. This cycle is then repeated twice. After the fourth passage through the punched bottom, a thread is obtained which is positioned on a ceramic bar and sintered. To do this, the string is heated in a tube furnace by 1.5 K/min to reach 400° C. and then by 5 K/min to reach 1,380° C. At this temperature, sintering proceeds for one hour. The sintered $^{90}SrTiO_3$ thread can be manipulated, but is brittle and has a density of approx. 4.1 g/cm$^3$. It is now cut into cylinders having a length of 1.8 mm. The resulting pieces are encapsulated in small stainless steel tubes, whereby two small tantalum cylinders of the same diameter as the thread are inserted in front of and behind the cylindrical $^{90}SrTiO_3$ radiation source, respectively.

What is claimed is:

1. A method for producing highly radioactive, miniaturized ceramic strontium 90 radiation sources, which comprises:

mixing 1) an aqueous solution of a strontium 90 nitrate salt or a strontium 90 salt of an organic acid, 2) a solution containing at least one compound selected from the group consisting of a titanium alkoxide, a zirconium alkoxide and a silicon alkoxide, and 3) an ammonium salt of at least one acid selected from the group consisting of carbonic acid and organic acid;

expelling the solvent to form a residue;

calcining the residue to form a powder;

adding at least one auxiliary agent for plastication, wherein the auxiliary agent is at least one material selected from the group consisting of a cellulose derivative, a polysaccharide, a polyol and a polyelectrolyte;

transforming the residue into a plastic mass;

microextruding the plastic mass to form a thread;

sintering the thread; and cutting the thread, whereby a cylinder is obtained.

2. The method according to claim 1, wherein the titanium compound is tetraisopropyl orthotitanate (TiPOT).

3. The method according to claim 1, wherein the silicon compound is tetraethoxysilane (TEOS).

4. The method according to claim 1, wherein the zirconium compound is zirconium (IV) propoxide.

5. The method according to claim 4, wherein the mol ratio of $^{90}Sr:Me:NH_4$ is 0.85–1:0.95–1.05:1.7–2, wherein Me is Ti, Zr and/or Si.

6. The method according to claim 1, wherein expelling the solvent is accomplished by evaporation and/or sublimation.

7. The method according to claim 1, wherein the calcining is performed at a temperature ranging between 650–1,000° C.

8. The method according to claim 1, wherein organic auxiliary agents for plastication are added to the calcined powder in an amount ranging between 6 and 18 percent by weight in relation to the powder.

9. The method according to claim 8, wherein in addition to the organic agents, a Me-alkoxide is added to the calcined powder in an amount ranging between 0.5 and 2 percent by weight in relation to the powder, wherein Me means Ti, Zr and/or Si.

10. The method according to claim 1, wherein the sintering temperature is between 1,260° C. and 1,420° C.

11. The method according to claim 1, wherein after expelling the solvent, the residue is freeze-dried to form a lyophilisate; and the lyophilisate is calcined.

12. The method according to claim 1, wherein the cylindrical radiation sources obtained are encapsulated.

13. The method according to claim 12, wherein said encapsulation is brought about by inserting the radiation source into a tube which is closed on one end and sealing the opening on the other end by means of a lid.

14. The method according to claim 13, wherein, before sealing, first and second tantalum cylinders having the same diameter as the radiation source are inserted into the tube, whereby the first cylinder is inserted in front of the cylindrical radiation source and the second cylinder is inserted behind the cylindrical radiation source.

15. The method according to claim 1, wherein the alkoxide is at least one alkoxide selected from the group a consisting of ethoxide, propoxide, butoxide, isoethoxide, isopropoxide and isobutoxide.

16. The method according to claim 1, wherein the calcining is performed at a temperature ranging between about 800–830° C.

17. The method according to claim 1, wherein the sintering temperature is between about 1,370° C. and 1,390° C.

18. The method according to claim 5, wherein the mol ratio of $^{90}Sr:Me:NH_4$ is 0.93:1:1.86, wherein Me means Ti, Zr and/or Si.

* * * * *